US006572873B1

(12) United States Patent
Osman et al.

(10) Patent No.: US 6,572,873 B1
(45) Date of Patent: Jun. 3, 2003

(54) GENERATION OF THERAPEUTIC MICROFOAM

(75) Inventors: Tariq Osman, London (GB); Sheila Bronwen Flynn, Nr. Stevenage (GB); David Dakin Iorwerth Wright, High Wycombe (GB); Anthony David Harman, Checkendon (GB); Timothy David Boorman, Frinton on Sea (GB)

(73) Assignee: BTG International Limited, London (GB); part interest ( * ) Notice: Subject to any disclaimer, the term of this patent is extended or adjusted under 35 U.S.C. 154(b) by 0 days.

(21) Appl. No.: 09/718,094

(22) Filed: Nov. 22, 2000

Related U.S. Application Data (63) Continuation of application No. PCT/GB00/02045, filed on May 26, 2000.

(30) Foreign Application Priority Data

May 26, 1999 (GB) ............................................. 9912356

(51) Int. Cl.⁷ ............................. A61K 9/08; A61K 9/12; A61F 13/36
(52) U.S. Cl. ........................ 424/423; 424/423; 424/43; 424/9.5; 424/9.51; 424/45; 424/47; 424/9.52; 424/46; 424/450; 424/484; 424/76.2; 514/724; 514/738; 514/706; 514/708
(58) Field of Search ............................. 424/43, 9.5, 44, 424/9.51, 45, 9.52, 47, 46, 450, 423, 76.2, 484; 514/724, 738, 706, 708

(56) References Cited

U.S. PATENT DOCUMENTS

| | | | |
|---|---|---|---|
| 3,970,219 A | 7/1976 | Spitzer et al. | |
| 4,019,657 A | 4/1977 | Spitzer et al. | |
| 4,127,131 A | 11/1978 | Vaillancourt | |
| 4,292,972 A | 10/1981 | Pawelchak et al. | |
| 4,466,442 A | 8/1984 | Hilmann et al. | |
| 5,064,103 A | 11/1991 | Bennett | |
| 5,542,935 A | 8/1996 | Unger et al. | |
| 5,623,085 A | * 4/1997 | Gebhard et al. | ............... 560/25 |
| 5,656,200 A | * 8/1997 | Boettcher et al. | ........... 252/307 |
| 5,676,962 A | * 10/1997 | Caberra Garrido et al. | ... 424/43 |

FOREIGN PATENT DOCUMENTS

| | | |
|---|---|---|
| DE | 3417182 C2 | 1/1989 |
| EP | 0 324 938 | 7/1989 |
| EP | 0656203 | 6/1995 |
| FR | 2672038 | 7/1992 |
| FR | 2775436 | 9/1999 |
| WO | 92/05806 | 4/1992 |
| WO | WO 99/43371 | 9/1999 |

OTHER PUBLICATIONS

Fluckiger, V., "Nicht–operative retrograde . . . ," Schweizerische Medizinishe Wochenshrift Nr. 48, and translation to English.

Brucke, H., "Angiologie: Zur Atiologie und Behandlung . . . ," Heft 4, 1957, and English language translation.

Meyers Konversations–Lexikon, 5.Aufl.5.Aufl., 1895, Bd. 15. S.386 Schaum . . . and English language tnraslation.

Binningen, Von Dr. K. Sigg, "Neuere Gesichtspunkte zur . . . ," Therapeutische Umschau, Bern. Dec. 1949, VI. Jahrgang, Heft. 9.

Prace Pogladowe, Wiad. Lek. 1973, XXVI, 19.

* cited by examiner

*Primary Examiner*—Russell Travers
*Assistant Examiner*—S Sharareh
(74) *Attorney, Agent, or Firm*—Nixon & Vanderhye

(57) ABSTRACT

Improved therapeutic sclerosing microfoams and methods and devices for making them are provided that have advantage in producing a consistent profile injectable foam with minimal input by the physician yet using high volume percentages of blood dispersible gases, thus avoiding use of potentially hazardous amounts of nitrogen.

19 Claims, 8 Drawing Sheets

GENERATION OF THERAPEUTIC MICROFOAM

This is a continuation of PCT application No. PCT/GB00/02045, filed May 26, 2000, the entire content of which is hereby incorporated by reference in this application.

The present invention relates to the generation of microfoam comprising a sclerosing material, particularly a sclerosing liquid, which is suitable for use in the treatment of various medical conditions involving blood vessels, particularly varicose veins and other disorders involving venous malformation. Sclerosis of varicose veins is based on the injection into the veins of liquid sclerosant substances which, by inter alia causing a localized inflammatory reaction, favor the elimination of these abnormal veins. When a sclerosing substance is injected in liquid form, it is mixed with the blood contained in the vein and is diluted in an unknown proportion. The results are uncertain, owing to over- or under-dosage, and are limited to short varicose segments. As the size of the various veins to be injected decreases, this dilution is less and the results obtained are more predictable.

Until recently, sclerosis was a technique selected in cases of small and medium varicose veins, those with diameters equal to or greater than 7 mm being treated by surgery. Sclerosis and surgery complemented one another but sclerosis treatment continued not to be applicable to large varicose veins. In these large varicose veins, if a sclerosing substance was injected, its concentration in the vein, its homogenous distribution in the blood, and the time for which it is in contact with the internal walls of the vessel treated were not known.

In 1946, Orbach injected a few cubic centimeters of air into small varicose veins and confirmed a displacement of the blood inside the vessel which was occupied by the injected air. A sclerosing solution introduced immediately afterwards was more effective than if it had been injected into the blood. However, in thick varicose veins, when air is injected the phenomenon described of the displacement of the blood by the injected air does not occur but the air forms a bubble inside the vein which makes the method ineffective in these vessels.

The same author had the idea, a few years later, of injecting foam obtained by agitation of a container containing sodium tetradecyl sulfate, which is an anionic sclerosing detergent with a good foaming capability. The method was of little use owing to the large size of the bubbles formed and was dangerous owing to the side effects of atmospheric nitrogen which is only slightly soluble in blood. Both methods had limited practical repercussion being used only in small various veins.

An injectable microfoam suitable for therapeutic uses has now been developed and is described in EP 0656203 and U.S. Pat. No. 5,676,962 (incorporated herein by reference). These patents describe a microfoam produced with a sclerosing substance which, when injected into a vein, displaces blood and ensures that the sclerosing agent contacts the endothelium of the vessel in a known concentration and for a controllable time, achieving sclerosis of the entire segment occupied.

The advantage of use of this foam are that it allows the concentration of the sclerosing agent in the blood vessel to be known, since the microfoam displaces the blood and is not diluted therein in to the same extent as a simple liquid would be. Furthermore it allows homogenous distribution of the sclerosis product in the vein to be ensured and the time for which it is kept in contact with the internal walls of the vein to be controlled. None of which factors is known precisely or is controllable with the use of sclerosing agents in simple liquid form.

The preparation of such a microfoam may be carried out with a solution of any sclerosing substance, particularly polidocanol, alkali metal tetradecyl sulfate e.g. sodium salt, hypertonic glucose or gluco-saline solutions, chromic glycerol, ethanolamine oleate, sodium morrhuate or iodic solutions.

However, this known method requires production of microfoam by the physician, pharmacist or an assistant immediately prior to administration to the patient. Such procedure allows for variation of agent depending upon the person preparing it, with content of gas, bubble size and stability all needing attention with respect to the condition being treated. It also requires a high degree of care and knowledge that may be difficult to replicate under pressure, i.e. when time available to prepare the foam is short.

The method particularly described in the aforesaid patents uses a high speed beating action with a brush to generate a foam of correct property. Other reported techniques in use do not produce such uniform, stable or injectable microfoam and notably includes these where gas is bubbled, e.g. sparged into the sclerosant, e.g. by leakage into a sclerosant filled syringe from around the side of the syringe plunger.

Furthermore, a problem in using air as the gas for producing the foam is the perception that large volumes of nitrogen should not unnecessarily be introduced into patients, particularly where large vessels are being filled with foam and eliminated. Gas embolism with nitrogen remains a possibility.

The solubility of physiological gases in aqueous fluids, such as blood, varies considerably. Thus while nitrogen is almost twice as insoluble in water as oxygen at STP, carbon dioxide is over fifty times as soluble in aqueous liquids as nitrogen and over twenty five times as soluble as oxygen.

TABLE 1

Solubility of Gases in water at STP

| Gas | Mole Fraction Solubility $10^{-5}$ |
| --- | --- |
| Helium | 0.7 |
| Nitrogen | 1.18 |
| Oxygen | 2.3 |
| Xenon | 7.9 |
| Nitrous oxide | 43.7 |
| Carbon dioxide | 61.5 |

At the present time it is perceived that production of such microfoam with gases incorporating high proportions of gas that is readily dispersed in blood, such as carbon dioxide, would be desirable for the purposes of minimizing the prospect of the treatment producing a gas embolism. However, it is also perceived by practitioners that this is difficult task due to its high solubility in water.

It would also be desirable to provide a relatively stable microfoam of uniform character that is readily producible by use of a relatively simple and reliable mechanism, rather than one involving use of high speed mixing or beating, the time of performance of which may affect foam property.

It is particularly desirable that the microfoam so produced may be passed through a needle of gauge suitable for injecting into blood vessels without being significantly converted back to its separate gas and liquid components and/or changing characteristics such as significantly increasing bubble sizes.

Such a needle may be of very small diameter, e.g. a 30 gauge needle (0.14 mm interior diameter). More typically it will be larger e.g. an 18 to 22 gauge needle (interior diameter 0.838 to 0.394 mm), more preferably 19 to 21 gauge (interior diameter 0.686 mm).

The rate at which the foam is passed down the needle can be such that any foam might be broken down, but it is desirable that a foam is produced that does not break down under normal injection conditions, i.e. at rates compatible with control of entry of foam into a vein. For example, it should be withstand injection at rates of 0.1 to 0.5 mL/second, more preferably 0.3 to 1 mL/second for a 19 to 21 gauge needle.

It is still further desirable to provide a device that is of sterile type with regard to the foam it generates particularly with regard to micro-organisms and pyrogens.

It is particularly desirable to provide a sealed device that operates to produce foam of set property suitable for a given medical procedure without technical input from the physician who will perform the procedure, or assistants thereof.

One foam of device that could potentially provide these desired properties would be an aerosol dispenser of a type that produces foams. However, for the purposes of generating a microfoam to be injected into a human or animal body, it is undesirable to have a propellant gas of the type usually employed in aerosol canisters, e.g. such as isopropane. This determines that the gas from which the foam is to be made must itself be pressurized to allow production of foam.

Water soluble gases such as carbon dioxide have been found by the inventors to be incapable of producing a stable foam when generated by merely being passed through a standard aerosol valve under pressure, such as might be expected to convert a detergent solution such as one of polidocanol or sodium tetradecylsulfate to a foam. They have determined that when this gas is used under pressure to propel a sclerosing agent solution through a conventional aerosol valve the foam produced, while initially containing at least some microfoam structure, is not sufficiently stable to be applied to the treatment of blood vessels as described in EP 0656203 and U.S. Pat. No. 5,676,962. Such foam is furthermore incapable of being passed through a syringe needle without significant reversion to liquid and gas phases. It will be realized by those skilled in the art that the microfoam technique exploits the ability of the gas to deliver the sclereosant solution to the wall of the vessel to be treated, rather than to allow its dilution in blood as in the liquid phase.

Aerosal units that are capable of producing foam have been described in the prior art. U.S. Pat. No. 3,471,064 describes a device wherein air is drawn into a foamable liquid through a series of small holes in the dip tube of the unit. Such a device is not sterile in operation as it relies on its contents being open to the air. Foam so produced would appear to vary in properties dependent upon how much air is drawn in. A further device is described in U.S. Pat. No. 3,428,222 and utilizes a wicking and foaming element in a compressible container that again draws in air to produce foam.

U.S. Pat. No. 3,970,219 describes sealed aerosol devices which are capable of using pharmacologically inert gases to foam and expel liquid compositions, It describes devices which produce foam by passage of the propellant through a material having pores of 0.01 to 3 mm diameter from a lower propellant gas holding chamber to an upper foam holding chamber. The liquid to be foamed sits in the upper chamber or is absorbed onto the porous material by shaking the container or is wicked up from a lower chamber. This patent teaches that liquid from foam in the upper chamber drains down into the lower chamber, such that the thinnest walled bubbles are expelled, and teaches that the propellant gas should be 'less soluble', such as nitrogen, fluorocarbon or hydrocarbon, where aqueous liquids are to be foamed.

Similar bubbler devices are used in accessories for use with 'environmentally friendly' aerosol devices that operate using air under low pressure, i.e. hand pump conditions. Two such devices are supplied by Airspray International as the 'Airspray™ Finger Pump Foamer' and 'Airspray Mini-Foamer'. The former is said to be suitable for simple water based formulations while the latter is suggested for cosmetics, hair or skin care preparations. A second such device is provided as an optional extra in the Swedspray/Eurospray™ hand pump device as a foaming nozzle. This device is marketed as being suitable for use to 'make your own cleansing foam or shaving lather'.

However, the present inventors have found that use of the available hand-pump devices themselves, which in any case are not sterile, cannot produce good microfoam with high loadings of carbon dioxide due to outgassing, nor with inclusion of significant amounts of glycerol which otherwise stabilizes microfoam. Furthermore, when significant back-pressure is applied to the outlet of such device, such as when attached to a syringe to be loaded for injecting the foam, stuttering occurs. Use of low ejection velocity with this device can cause wetting at the nozzle which results in large bubbles caused by air entrapment. In any case the foams so produced, whether with oxygen or carbon dioxide, tend to be very dry, with resultant need for high concentration of sclerosant to be included, and tendency to break up on passage down a needle.

It is preferred not to unnecessarily use high concentrations of sclerosant in the solution as this could result in overdosage should a dispensing device fail and deliver as more dense microfoam, i.e. including a higher proportion of liquid than intended.

Thus there is a need to provide a method and device that are capable of producing a uniform injectable microfoam made with a relatively low concentration of a sclerosing agent and a significant amount of blood dispersible gas in sterile fashion without volatile liquid propellants or the need for the operator to directly be concerned in control of its parameters.

The present applicants have now provided a method and devices capable of addressing at least some of the aforesaid needs and have produced a novel stable injectable sclerosing microfoam with that method and devices.

For the purpose of this application terms have the following definitions: Physiologically acceptable blood dispersible gas is a gas that is capable of being substantially completely dissolved in or absorbed by blood. A sclerosant liquid is a liquid that is capable of sclerosing blood vessels when injected into the vessel lumen. Scleropathy of sclerotherapy relates to the treatment of blood vessels to eliminate them. An aerosol is a dispersion of liquid in gas. A major proportion of a gas is over 50% volume/volume. A minor proportion of a gas is under 50% volume/volume A minor amount of one liquid in another liquid is under 50% of the total volume. Atmospheric pressure and bar are 1000 mbar gauge. Half-life of a microfoam is the time taken for half the liquid in the microfoam to revert to unfoamed liquid phase.

In a first aspect of the present invention there is provided a method for producing a microfoam suitable for use in scleropathy of blood vessels, particularly veins, characterized in that it comprises passing a mixture of a physiologically acceptable blood dispersible gas and an aqueous sclerosant liquid through one or more passages having at least one cross-sectional dimension or from 0.1 to 30 μm, the ratio of gas to liquid being controlled such that a microfoam is produced having a density of between 0.07 g/mL to 0.19 g/mL and a half-life of at least 2 minutes.

Preferably the microfoam is such that 50% of more by number of its gas bubbles of 25 μm diameter and over are no more than 200 μm diameter.

Preferably the gas/liquid ratio in the mix is controlled such that the density of the microfoam is 0.09 g/mL to 0.16 g/mL, more preferably 0.11 g/mL to 0.14 g/mL.

Preferably the microfoam has a half-life of a least 2.5 minutes, more preferably at least 3 minutes. The half-life may be as high as 1 or 2 hours or more, but is preferably less than 60 minutes, more preferably less than 15 minutes and most preferably less than 10 minutes.

Half-life is conveniently measured by filling vessel with a known volume and weight of foam and allowing liquid from this to drain into a graduated vessel, the amount drained in a given time allowing calculation of half-life i.e. of conversion of microfoam back into its component liquid and gas phases. This is preferably carried out at standard temperature and pressure, but in practice ambient clinic or laboratory conditions will suffice.

Advantageously and preferably the method provides a foam characterized in that at least 50% by number of its gas bubbles of 25 μm diameter and over are of no more than 150 μm diameter, more preferably at least 95% of these gas bubbles by number are of no more than 280 μm diameter. Still more preferably at least 50% by number of these gas bubbles are of no more than 130 μm diameter and still more preferably at least 95% of these gas bubbles by number are of no more than 250 μm diameter.

Preferably the mixture of gas and sclerosant liquid is in the form of an aerosol, a dispersion of bubbles in liquid or a macrofoam. By macrofoam is meant a foam that has gas bubbles that are measured in millimeters largest dimension, e.g. approximately 1 mm and over, and over such as can be produced by lightly agitating the two phases by shaking. Preferably the gas and liquid are in provided in the form of an aerosol where a source of pressurized gas and a means for mixing the two is provided to the point of use. It may be preferred that a macrofoam is first produced where the liquid and gas are brought together only at the point of use.

The ratio of gas to liquid used in the mixture is important in order to control the structure of the microfoam produces such that its stability of optimized for the procedure and the circumstances in which it is being carried out. For optimum foams it its preferred to mix 1 gram sclerosant liquid with from approximately 6.25 to 14.3 volumes (STP), more preferably 7 to 12 volumes (STP), of gas.

Preferably the physiologically acceptable blood dispersible gas comprises a major proportion of carbon dioxide and/or oxygen. Conveniently it may comprise a minor proportion of nitrogen or other physiologically acceptable gas. While a proportion of nitrogen may be present, as in air, the present invention provides for use of carbon dioxide and/or oxygen without presence of nitrogen.

In one preferred form the gas used is a mixture of carbon dioxide and other physiological gases, particularly containing 3% or more carbon dioxide, more preferably from 10 to 90% carbon dioxide, most preferably 30 to 50% carbon dioxide. The other components of this gas are preferably oxygen with a minor proportion only of nitrogen being preferred. Most preferably the other component is oxygen.

A further preferred form of gas comprises 50% vol/vol or more oxygen, the remainder being carbon dioxide, or carbon dioxide, nitrogen and trace gases in the proportion found in atmospheric air. One preferred gas is 60 to 90% vol/vol oxygen and 40 to 10% vol/vol carbon dioxide, more preferably 70 to 80% vol/vol oxygen and 30 to 20% vol/vol carbon dioxide. More preferred is 99% or more oxygen.

It is found that passing a stream of the sclerosant liquid and the gas under pressure through one or more passages of 0.1 μm to 30 μm as described provides a stable blood dispersible gas based sclerosant injectable microfoam that was previously thought to be only producible by supply of high amounts of energy using high spread brushes and blenders.

Preferably the sclerosing agent is a solution of polidocanol or sodium tetradecylsulfate in an aqueous carrier, e.g. water, particularly in a saline. More preferably the solution is from 0.5 to 5% v/v polidocanol, preferably in sterile water or a physiologically acceptable saline, e.g. in 0.5 to 15% v/v saline. Concentration of sclerosant in the solution will be advantageously increased for certain abnormalities such as Klippel-Trenaunay syndrome.

Polidocanol is a mixture of monolauryl ethers of formula $C_{12}H_{25}(OCH_2CH_2)_nOH$ with an average value of n of 9. It will be realized that mixtures with other alkyl chains, oxyalkyl repeat units and/or average values of n might also be used, e.g. 7 to 11, but that 9 is most conveniently obtainable, e.g. from Kreussler, Germany, e.g. Aethoxysklerol™.

Most preferably the concentration of sclerosant in the aqueous liquid is a 1–3% vol/vol solution, preferably of polidocanol, in water or saline, more preferably about 2% vol/vol. The water or saline also, in some cases at least, preferably contain 2–4% vol/vol physiologically acceptable alcohol, e.g. ethanol. Preferred saline is buffered. Preferred buffered saline is phosphate buffered saline. The pH of the buffer is preferably adjusted to be physiological, e.g. from pH 6.0 to pH 8.0, more preferably about pH 7.0

The sclerosant may also contain additional components, such as stabilizing agents, e.g. foam stabilizing agents, e.g. such as glycerol. Further components may include alcohols such as ethanol.

The aerosol, dispersion or macrofoam is preferably produced by mixing the gas and liquid from respective flows under pressure. The mixing conveniently is carried out in a gas liquid interface element such as may be found in aerosol canisters. The interface device may however be very simple, such as a single chamber or passage of millimeter dimensions, i.e. from 0.5 to 20 mm diameter, preferably 1 to 15 mm diameter, into which separate inlets allow entry of gas and liquid. Conveniently the interface is of design which is commonly found in aerosol canisters but which is selected to allow the correct ratio of gas to liquid to allow formation of a foam of the presently defined density. Suitable inserts are available from Precision Valves (Peterborough UK) under the name Ecosol and are selected to produce the ratio specified by the method above.

However, the mixing of gas and liquid may also be brought about within a dip-tube leading from the sclerosant solution located in the bottom of a pressurized container where holes in the dip-tube allow gas to enter into a liquid stream entering from the bottom of the tube. In this case the holes may be of similar diameter to the Ecosol holes. Such holes may be conveniently produced by laser drilling of the dip-tube.

The one or more passages through which the aerosol or macrofoam so produced are passed to produce the stable microfoam preferably have diameter of from 5 μm to 25 μm preferably from 10 μm to 20 μm where simple passages are provided, such as provided by openings in a mesh or screen, e.g. of metal or plastics, placed perpendicular to the flow of gas/liquid mixture. The passage is conveniently of circular or elliptical cross section, but is not necessarily so limited. A number of such meshes or screens may be employed along the direction of flow.

Most preferably the passages are provided as multiple openings in one or more elements placed across the flow. Preferably the elements are from 2 to 3 mm diameter, more preferably 6 to 15 mm diameter, face on to the flow, with 5 to 63% open area, e.g. 2% to 20% open for woven meshes and 20% to 70% open area for microporous membranes. Openings in a porous material, such as provided in a perforated body, preferably provide several hundreds or more of such passages, more preferably tens or hundred of thousands of such passages, e.g. 10,000 to 500,000, presented to the gas liquid mixture as it flows. Such material may be a perforated sheet or membrane, a mesh, screen or sinter. Still more preferably a number of sets of porous material are provided arranged sequentially such that the gas and liquid pass through the passages of each set. This leads to production of a more uniform foam.

Where several elements are used in series these are preferably spaced 1 to 5 mm apart, more preferably 2 to 4 mm apart e.g. 3 to 3.5 mm apart.

For some embodiments of the present invention it is found that the passage may take the form of a gap between fibers in a fibrous sheet placed across the path of the gas/liquid flow, and the dimension described in not necessarily the largest diameter, but is the width of the gap through which the gas/liquid aerosol or macrofoam must flow.

Alternatively the method provides for passing the mixture of gas and liquid through the same set of passages, e.g. as provided by one or more such porous bodies, a number of times, e.g. from 2 to 2,000, more preferably 4 to 200 times, or as many times as conveniently results in a microfoam of the required density set out above. It will be realized that the more times the microfoam passes through the meshes, the more uniform it becomes.

The pressure of gas used as it is passed through the passages will depend upon the nature of the mechanism used to produce the foam. Where the gas is contained in a pressurized chamber, such as in an aerosol canister, in contact with the liquid, suitable pressures are typically in the range 0.01 to 9 bar over atmosphere. For use of meshes, e.g. 1 to 8 meshes arranged in series, having apertures of 10–20 $\mu$m diameter, 0.1 to 5 bars over atmosphere will, inter alia, be suitable. For use of 3–5 meshes of 20 $\mu$m aperture it is found that 1.5–1.7 bar over atmospheric is sufficient to produce a good foam. For a 0.1 $\mu$m pore size membrane, a pressure of 5 bar or more over atmospheric pressure is preferred.

In one preferred form of the invention the passages are in the form of a membrane, e.g. of polymer such as polytetrafluoroethylene, wherein the membrane is formed of randomly connected fibers and has a rated effective pore size which may be many times smaller than its apparent pore size. A particularly suitable form of this is a biaxially oriented PTFE film provided by Tetratec™ USA under the trademark Tetratex™, standard ratings being 0.1 to 10 $\mu$m porosity. Preferred pore sizes for the present method and devices are 3 to 7 $\mu$m. This material may be laminated with a porous backing material to give it stength and has the advantage that one pass through may be sufficient to produce a foam that meets the use requirements set out above with regard to stability. However, it will evident to those skilled in the art that use of more than one such membrane in series will give a still more uniform foam for given set of conditions.

It is believed that the combination of provision of a stream of solution and gas under pressure through an aerosol valve and then flow through the passages, e.g. pores in a mesh screen, membrane or sinter provides energy sufficient to produce a stable aqueous liquid soluble gas, e.g. carbon dioxide and/or oxygen, based sclerosant microfoam that was previously thought to be only producible by supply of high amounts of energy using high speed brushes and blenders as described in the prior art.

Preferably the method of the invention provides a microfoam having at least 50% by number of its gas bubbles of 25 $\mu$m diameter or over being no more than 120 $\mu$m diameter. Preferably at least 95% of its gas bubbles of 25 $\mu$m diameter or over are of no more than 250 $\mu$m diameter. Diameter of such bubbles may be determined by the method set out in the Example 5 set out herein.

A most preferred method of the invention provides a housing in which is situated a pressurisable chamber. For sterile supply purposes this will at least partly filled with a sterile and pyrogen free solution of the sclerosing agent in a physiologically acceptable aqueous solvent but otherwise may be charged with such at the point of use. This convenient method provides a pathway by which the solution may pass from the pressurisable chamber to exterior of the housing through an outlet and more preferably a mechanism by which the pathway from the chamber to the exterior can be opened or closed such that, when the container is pressurized, fluid will be forced along the pathway and through one or more outlet orifices.

The method is particularly characterized in that the housing incorporates one or more of (a) a pressurized source of the physiologically acceptable gas that is readily dispersible in blood, and (b) an inlet for the admission of a source of said gas; the gas being contacted with the solution on activation of the mechanism.

The gas and solution are caused to pass along the pathway to the exterior of the housing through the one or more, preferably multiple, passages of defined dimension above, through which the solution and gas must pass to reach the exterior, whereby on contact with, e.g. flow through, the passages the solution and gas form a the microfoam.

Preferably the gas and liquid pass through the gas liquid interface mechanism, typically being a junction between a passage and one or more adjoining passages, and are converted to an aerosol, dispersion of bubbles or macrofoam before passing through the passages, but as explained they may be converted first to a macrofoam, e.g. by shaking of the device, e.g., by hand, or mechanical shaking device.

In a second aspect of the present invention there is provided a device for producing a microfoam suitable for use in scleropathy of blood vessels, particularly veins, comprising a housing in which is situated a pressurizable chamber containing a solution of the sclerosing agent in a physiologically acceptable solvent referred to in the first aspect; a pathway with one or more outlet orifices by which the solution may pass from the pressurisable chamber to exterior of the device through said one or more outlet orifices and a mechanism by which the pathway from the chamber to the exterior can be opened or closed such that, when the container is pressurized and the pathway is open, fluid will be forced along the pathway and through the one or more outlet orifices said housing incorporating one or more of (a) a pressurized source of physiologically acceptable gas that is dispersible in blood and (b) an inlet for the admission of said gas; the gas being in contacted with the solution on activation of the mechanism such as to produce a gas solution mixture said pathway to the exterior of the housing including one or more elements defining one or more passages of cross sectional dimension, preferably diameter, 0.1 μm to 30 μm, through which the solution and gas mixture is passed to reach the exterior of the device, said passing of said mixture through the passages forming a microfoam of from 0.07 to 0.19 g/mL density and of half-life at least 2 minutes.

Preferably the microfoam has 50% or more by number of its gas bubbles of 25 μm diameter and over of no more than 200 μdiameter.

More preferably the microfoam is from 0.09 to 0.16 g/mL density and most preferably of 0.11 g/mL to 0.14 g/mL.

Preferably the microfoam has a half-life of at least 2.5 minutes, more preferably at least 3 minutes.

Advantageously and preferably this device provides a microfoam characterized in that at least 50% by number of its gas bubbles of 25 μm diameter and over are of no more than 150 μm diameter or less, more preferably at least 95% by number of these gas bubbles are of diameter 280 μm or less. Still more preferably at least 50% by number of these gas bubbles are of no more than 120 μm diameter and still more preferably at least 95% of these gas bubbles are of no more than 250 μm diameter.

Preferably the apparatus includes a chamber, e.g. such as in a sealed canister, charged with the blood dispersible gas and the sclerosant liquid, e.g. in a single chamber, the device pathway including a dip tube with an inlet opening under the level of the liquid in this chamber when the device is positioned upright. Preferably the dip-tube has an outlet opening at gas liquid interface junction where the gas, which resides in the chamber above the liquid, has access to the pathway to the device outlet. The pathway is opened or closed by a valve element which is depressed or tilted to open up a pathway to the exterior of the device, whereby the liquid rises up the dip tube under gas pressure and is mixed in the interface junction with that gas to produce an aerosol, dispersion of bubbles in liquid or macrofoam.

Either inside the pressurisable chamber disposed in the pathway to the valve, or on the downstream side of the valve, is provided an element having the one or more passages described in the first aspect mounted such that the gas liquid mixture, i.e. dispersion of bubbles in liquid, aerosol or macrofoam, passes through the passage or passages and is caused to foam. This element may conveniently be located in a cap on the canister in between the valve mounting and an outlet nozzle. Conveniently depression of the cap operates the valve. Alternatively the element is within the canister mounted above the gas liquid interface.

In an alternate embodiment of the is device the gas liquid interface may comprise holes in the dip tube above the level of the liquid in the canister inner chamber.

The gas pressure employed will be dependent upon materials being used and their configuration, but conveniently will be 0.01 to 9 bar over atmospheric, more preferably 0.1–3 bar over atmospheric, and still more preferably 1.5–17 bar over atmospheric pressure.

A preferred device of this aspect of the invention is of the 'bag-on-valve' type. Such device includes a flexible gas and liquid tight container, forming a second inner chamber within the pressurisable chamber, which is sealed around the dip-tube and filled with the liquid. More preferably the dip-tube has a one-way valve located at a position between its end located in the sclerosant liquid and the gas liquid interface junction, which when the passage to the exterior is closed, remains closed such as to separate the liquid from the physiologically acceptable blood dispersible gas around it in the chamber. On opening the pathway to the exterior, the one way valve to also opens and release liquid up the dip-tube to the gas liquid interface where an aerosol is produced which is in turn then passed through the passages to be converted to microfoam. A suitable one-way valve is a duck-bill type valve, e.g. such as available from Vernay Labs Inc, Yellow Springs, Ohio, USA. Suitable bag-on-valve can constructions are available from Coster Aerosols, Stevenage, UK and comprise an aluminum foil/plastics laminate.

Conveniently the one way valve is located at the top of the dip-tube between that and the gas liquid interface junction, i.e. an Ecosol device. This allows filling of the bag before application of the one way valve, followed by sterilization of the contents, whether in the canister or otherwise.

Such a preferred device has several potential advantages. Where oxygen is the gas, this is kept separate from the liquid before use and thus reduces possibility of oxygen radicals reacting with organic components in the liquid, e.g. during sterilization processes such as irradiation. Where carbon dioxide is the gas, storage can lead to high volumes of gas dissolving in the liquid, which on release to the atmosphere or lower pressure, could out-gas and start to destroy the microfoam too quickly. Such separation also prevents the deposition of solidified sclereosing agent components in the dimension sensitive orifices of the device in an unused can in storage or transit, particularly should that be oriented other than upright.

It is preferred that the gas liquid interface is provided as a defined orifice size device such as the Ecosol device provided by Precision Valve Peterborough UK. For a device where the passages of defined dimension are outside of the pressurized chamber, i.e. mounted on the valve stem, the ratio of area of the gas holes to the liquid holes should be of the order of 3 to 5, preferably about 4. Where the passages are inside the pressurized chamber this is preferably higher.

A third aspect of the invention provides a device for producing a microfoam suitable for use in sclerotherapy of blood vessels, particularly veins, comprising a housing in which is situated a pressurisable chamber, at least part filled or fillable with a solution of a sclerosing agent in a physiologically acceptable solvent and/or a physiologically acceptable blood dispersible gas; a pathway by which the contents of the chamber may be passed to exterior of the housing through one or more outlet orifices and a mechanism by which the chamber can be pressurized such that its contents pass to the exterior along the pathway and through one or more outlet orifices said pathway to the exterior of the housing or the chamber including one or more elements defining one or more passages of cross sectional dimension, preferably diameter, 0.1 μm to 30 μm through which the contents of the chamber may be passed, whereby on passing through the passages the solution and gas form a microfoam of from 0.07 to 0.19 g/mL density and having a half-life of at least 2 minutes.

Preferably the microfoam is such that 50% or more by number of its gas bubbles of 25 μm or more diameter are of no more than 200 μm diameter.

Preferably the microfoam is of density 0.09 to 0.16 g/mL and more preferably of 0.11 g/mL to 0.14 g/mL. The preferred limits on bubble size are also as for the first and second aspects.

Preferably the microfoam has a half-life of at least 2.5 minutes, more preferably at least 3 minutes.

The elements defining the passages in the pathway or chamber may be static or may be movable by manipulation of the device from outside of its interior chamber.

Preferably the housing is a container defining a chamber in which is situated the solution and gas under pressure and the pathway is a conduit leading from the chamber in the interior of the container to a valve closing an opening in the container wall.

Preferred forms of the one or more elements defining the multiple passages for use in the device of the present invention are meshes, screens or sinters. Thus one or more meshes or perforated screens or sinters will be provided, with some preferred forms employing a series of such elements arranged in parallel with their major surfaces perpendicular to the path of solution/gas expulsion.

It is preferred that all elements of any of the devices according to the invention having a critical dimension are made of a material that does not change dimension when exposed to aqueous material. Thus element with such function such as the air liquid interface and the element defining the passages of 0.1 $\mu$m–30 $\mu$m dimension preferably should not be of a water swellable material such as Nylon 66 where they are likely to be exposed to the solution for more than a few minutes. Where such exposure is likely these parts are more preferably being fashioned from a polyolefin such as polypropylene or polyethylene.

Preferably the canister is sized such that it contains sufficient gas and solution to form up to 500 mL of microfoam, more preferably from 1 mL up to 200 mL and most preferably from 10 to 60 mL of microfoam. Particularly the amount of gas under pressure in such canisters should be sufficient to produce enough foam to treat, i.e. fill, at least one varicosed human saphenous vein. Thus preferred canisters of the invention may be smaller than those currently used for supply of domestic used mousse type foams. The most preferred canister device is disposable after use, or cannot be reused once opened such as to avoid problems of maintaining sterility.

It may be preferred to incorporate a device which maintains gas pressure in the canister as foam is expelled. Suitable devices are such as described under trademark devices PECAP and Atmosol. However, where a significant headspace or pressure of gas is provided this will not be necessary.

In order to ensure that the microfoam delivered from devices of the invention is not 'outside' specification, i.e. falls within the desired density, bubble size and half life parameters set out above, the present invention provides a further, fourth, aspect which provides a devices which is positioned to receive microfoam emitted from the device of the second and third aspects of the invention, which devices allows venting of the first portion of microfoam to waste and passage of a second portion of microfoam to a delivery device, such as a syringe, in sterile fashion.

A device of the fourth aspect comprises an inlet conduit being adapted to engage the outlet of a microfoam producing device of the second or third aspect in a microfoam tight fashion, the conduit being connected to and leading through a multipath tap capable of being set to direct microfoam passing down the conduit to one or both of first and second contiguous outlet conduits or to close the inlet conduit, at least one of the first and second outlets conduits being adapted to receive the luer connector of a syringe. Preferably the device is also comprises one or more elements for engaging the device of the second or third aspect other than by its outlet nozzle to hold it sercurely, e.g. upright in the case of a canister with a dip-tube.

Preferably the device of the fourth aspect comprises a three-way tap. More preferably the device of the fourth aspect comprises a base element, sufficiently stable to mount a microfoam producing device of the second or third aspects when engaged thereby. Preferably the microfoam producing device is engaged by resilient elements which locate it securely adjacent the three-way tap whereby the inlet conduit can be attached to the microfoam producing device outlet conduit.

Particularly preferred the device of the fourth aspect comprises a base element adapted mount the microfoam dispensing device and an activating element which operates to cause the pathway to be opened the to the inlet conduit. In this manner when the multi-way tap is shut, the dispensing device contents remain therein, but when the multi-way tap is opened to either of its outlet conduits it immediately causes release of foam generated by the device.

A further aspect of the present invention provides improved microfoams for use in the elimination of blood vessels and vascular malformations that are made available by the method and devices of the invention characterized in that they comprise a physiologically acceptable gas that is readily dispersible in blood together with an aqueous sclerosant liquid characterized in that the microfoam has a density of from 0.07 to 0.19 g/cm$^3$ and is capable of being passed down a 21 gauge needle without reverting back to gas and liquid by more than 10%, based on liquid content reverting back to unfoamed liquid phase.

Preferably the microfoam, on passage through said needle, does not revert back to unfoamed liquid by more than 5% based on liquid content, still more preferably by no more than 2%.

Preferably the microfoam is capable of being passed down a needle while retaining at least 50% by number of its gas bubbles of at least 25 $\mu$m diameter at no more than 200 $\mu$diameter. This is conveniently measured under ambient conditions, more preferably at STP.

Preferably at least 50% by number of said gas bubbles remain at no more than 150 $\mu$m diameter and at least 90% of these bubbles at no more than 250 $\mu$m diameter. Preferably the microfoam has a half-life as measured by drainage through a funnel of 2 cm neck diameter and drainage path 10 cm of at least 2 minutes, more preferably 2.5 minutes and most preferably 3 minutes. This may be carried out at ambient temperature of STP. Most conveniently the funnel is pre-equilibrated in a water bath to ensure a temperature of 25° C. before drying and application of foam. Placing of a microfoam filled syringe upside down, without its plunger, above the funnel leading into a graduated receptacle allows convenient measurement of this parameter.

Preferably the gas includes less than 40% v/v nitrogen. Preferably the density of the microfoam is from 0.09 to 0.16 g/mL, more preferably 0.11 g/mL to 0.14 g/mL.

Advantageously and preferably at least 50% by number of the gas bubbles of 25 $\mu$m diameter or more are of no more than 120 $\mu$m diameter and still more preferably at least 95% of these gas bubbles are of diameter 250 or less.

Preferably the foam density, which is a measure of liquid/gas ratio, is from 0.13 to 0.14 g/cm$^3$ and the half-life is at least 2.5 minutes. The foam more preferably does not move outside of its parameters of bubble size set out above in such time.

Preferably the gas consists of at least 50% oxygen or carbon dioxide, more preferably 75% or more oxygen or carbon dioxide and most preferably at least 99% oxygen or carbon dioxide, e.g. substantially 100% oxygen or carbon dioxide. Preferably the oxygen or carbon dioxide is medical grade.

Preferably the sclerosant is aqueous polidocanol or sodium tetradecyl sulfate.

When the sclerosant is aqueous polidocanol the concentration of polidocanol is from 0.5 to 4% vol/vol in the liquid, preferably being 1 to 3% vol/vol polidocanol and most preferably being 2% vol/vol in the liquid.

Advantageously the sclerosant is made up in water, but more advantageously is made up in a saline solution, particularly 10 to 70 mM phosphate buffer saline, e.g. 50 mM phosphate buffered saline, and preferably of pH 6 to pH 8.0 e.g. about pH 7.0. Advantageously the aqueous solution contains a minor amount of an alcohol, preferably 96% ethanol, e.g. at between 2 and 6% vol/vol, more preferably at about 4% vol/vol of 96% ethanol.

Addition of glycerol to the aforesaid sclereosant imparts a longer half-life to the resultant foam. However, glycerol also produces a tendency for the meshes to block up when using a mesh device as described above, so should be used carefully where the device it is produced from may be used multiple times or the bag-on-valve concept is used.

BRIEF DESCRIPTION OF THE DRAWINGS

The present invention will now be described further by way of illustration only by reference to the following Figures and Examples. Further embodiments falling within the scope of the invention will occur to those skilled in the art in the light of these.

EXAMPLES

Example 1

A standard aerosol canister with a one way depressible action valve is charged half full with a 3% v/v solution of polidocanol in sterile water and pressurized to 3 atmospheres with a 50:50 mix of carbon dioxide and oxygen. On the valve stem is mounted an actuator and delivery head which carries four plastics screens, just under 0.5 mm thick, perforated with 20 μm diameter passages, these screens being of the general type provided in the Swedspray-Eurospray foaming actuator cap ApRisC™ device. The valve is fed through an Ecosol gas liquid interface insert from a dip-tube and the surrounding chamber. Gas inlet sizes (×2) into the inserted are 0.006"×0.01" while the single liquid inlet is 0.024", as controlled by selecting Ecosol insert size. On depression of the head the aerosol valve release pre-mixed solution and gas onto the screens whereupon a microfoam suitable for scleropathy and that is dimensionally stable for at least 2 minutes, preferably 5 minutes using glycerol in the polidocanol solution is produced.

Example 2

Figure 1:
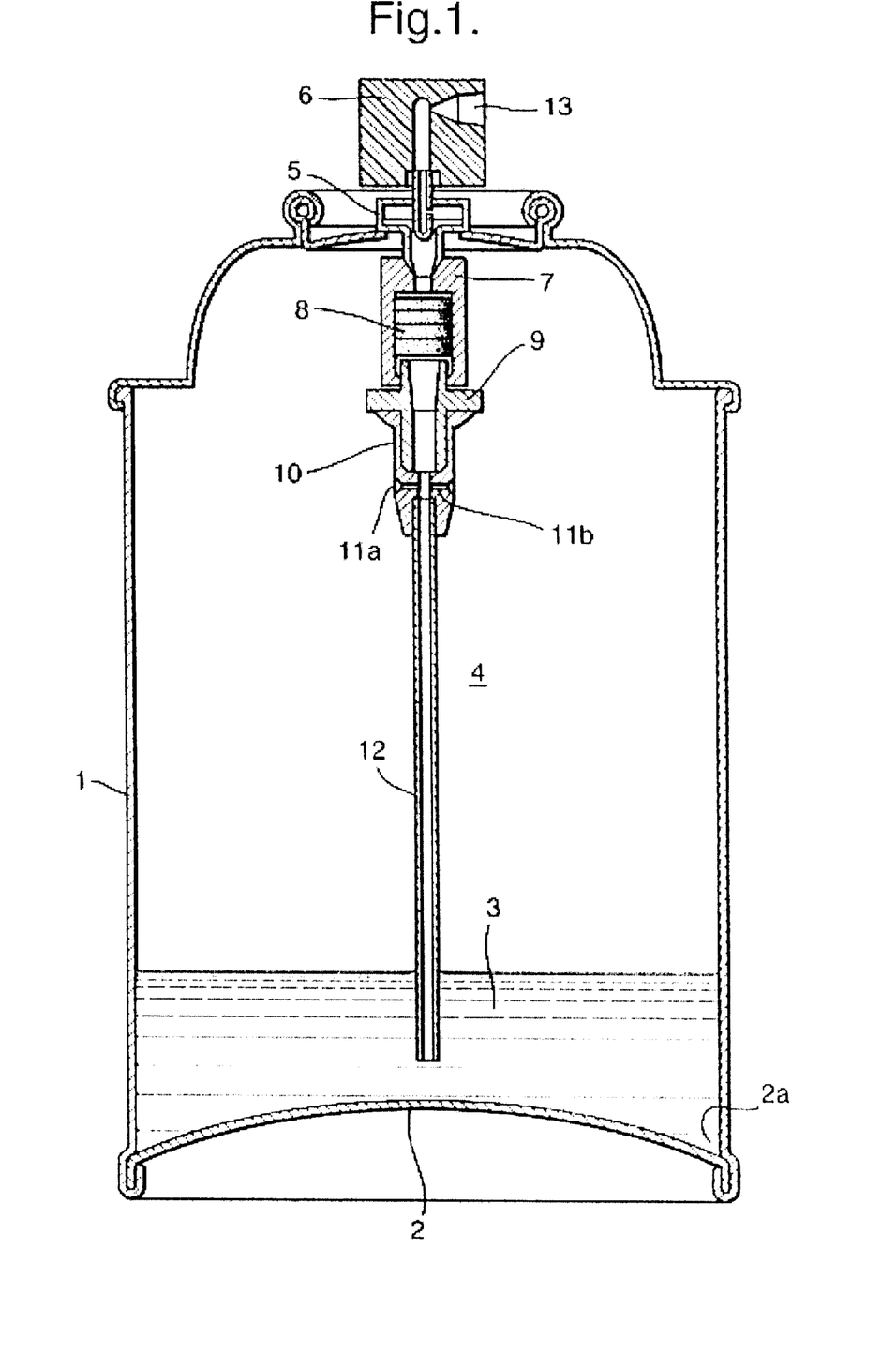
FIG. 1: Shows a cross-sectional view of a canister device of the second aspect of the invention as further described in Example 2 below.

FIG. 1 illustrates a further canister design of the invention wherein the passages through which the gas liquid mixture must travel are placed within the pressurized chamber, thus increasing hygiene of the device.

The canister is of standard 500 mL design with an aluminum wall (1), the inside surface of which is coated with an epoxy resin resistant to action of polidocanol and oxygen (e.g. Hoba 7940—Holden UK)). The bottom of the canister (2) is domed inward. The canister inner chamber (4) is pre-purged with 100% oxygen for 1 minute, containing 15 mL of a 2% vol/vol polidocanol/20 mmol phosphate buffered saline solution (3) then filled with the oxygen at 2.7 bar gauge (1.7 bar over atmospheric). This is provided by overpressuring the polidocanol part filled can with 1.7 bar oxygen.

The dome provides a perimeter area around the bottom of the inner chamber in which a level of polidocanol solution is retained sufficient for the bottom open end of a dip tube to be submerted therein when the top of the dome is no longer covered with the solution. In this manner, by use of an indicia on the outside of the canister to indicate the position of the dip tube, the canister can be oriented to extract the last fraction of solution if desired. In practice a vertical orientation is sufficient.

A standard 1" diameter aerosol valve (5) (Precision Valves, Peterborough) is crimped into the top of the canister after sterile part filling with the solution and is activatable by depressing an actuator cap (6) to release content via an outlet nozzle (13) sized to engage a luer fitting of a syringe or multi-way connector (not shown). A further connector (7) locates on the bottom of the standard valve and mounts, preferably by interference fit, four Nylon 66 meshes held on high density polyethylene (HDPE) rings (8) all within an open ended polypropylene casing. These meshes have diameter of 8 mm and have a 15% open area made up of 20 μm pores, with the meshes spaced 3.5 mm apart by the HDPE rings.

A further connector (9) locates on the bottom of the connector being holding the meshes and receives a housing (10) which mounts the dip tube (12) and includes gas receiving holes (11a, 11b) which admit gas from chamber (4) into the flow of liquid which rises up the diptube on operation of the actuator (6). These are conveniently defined by an Ecosol device with insert as before. Holes (11a, 11b) have cross-sectional area such that the sum total ratio of this to the cross-sectional area of the diptube is controlled to provide the required gas/liquid ratio. This is for example 0.010"×0.013" each hole (11a, 11b) to 0.040" liquid receiving hole.

Example 3

Figure 2:
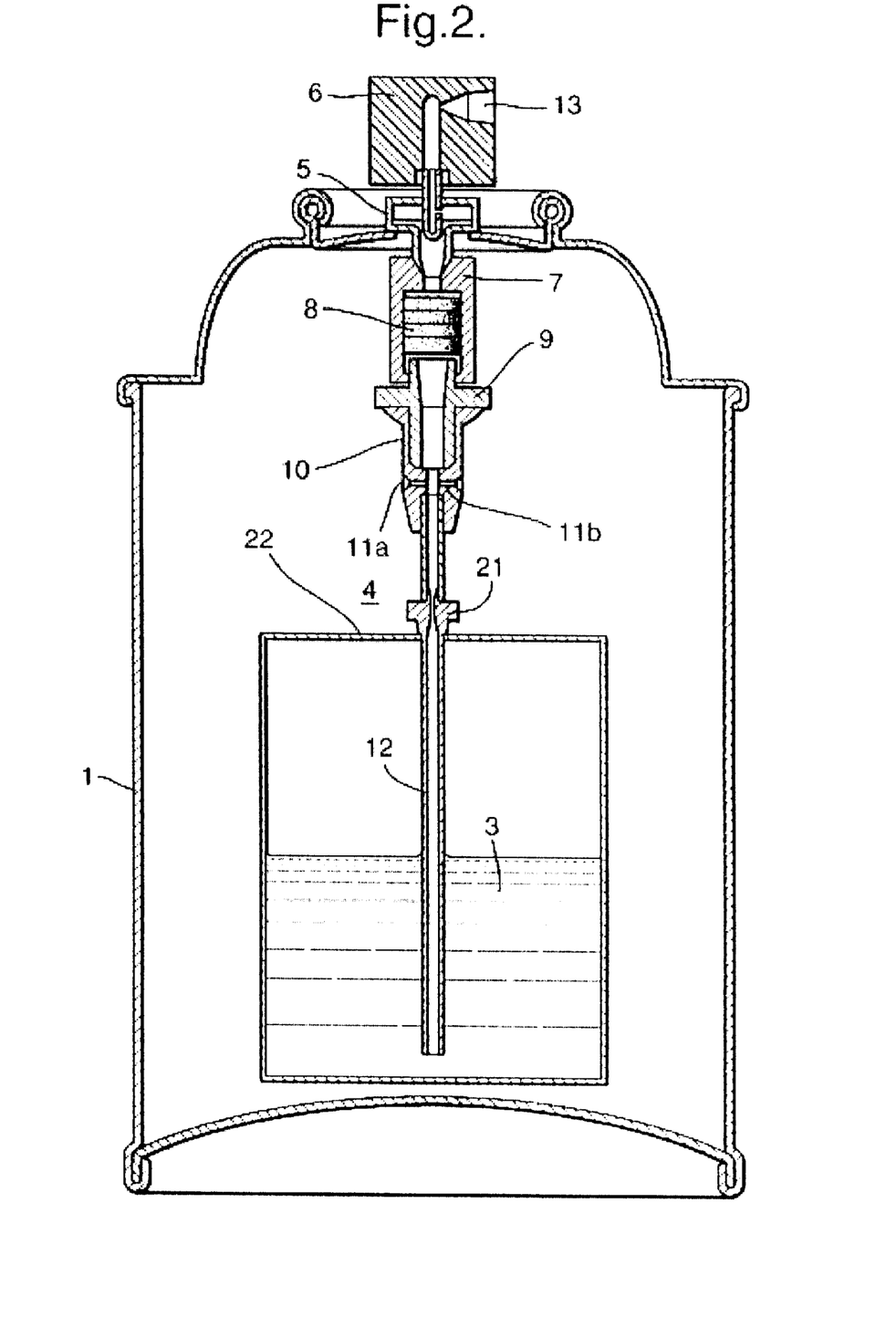
FIG. 2: Shows a cross-sectional view of a canister device of the second aspect incorporating a bag-on-valve reservoir for the sclerosant with the gas being in the outer chamber and separated therefrom by a one way duck-bill valve.

A further canister embodiment of the present invention is shown in FIG. 2, which is broadly as shown in FIG. 1, but for the inclusion of a modified 'bag-on-valve' arrangement. In this embodiment the polidocanol sclerosing solution (3) is enclosed in a foil bag (22), comprising an aluminum foil/plastics laminate (Coster Aerosols Stevenage UK) sealed in gas tight fashion to dip-tube (12). At the top end of the dip-tube is a one-way duck-bill valve (vernay Labs Inc Ohio USA) that serves to prevent contact of polidocanol with the contents of the dip-tube (12) and chamber (4) until the valve (5) is operated. On said operation the valve (21) opens and polidocanol solution (3) is caused to rise up the dip-tube (12), whereby it becomes mixed with the air/oxygen gas mixture entering through holes (11a, 11b). In this manner the can may be safely sterilized with ionizing radiation which may otherwise cause interactions between radical species in the gas and the organic component of the polidocanol solution. Such arrangement can also improve the operation of the canister with regard to start up of foam delivery. The bag (22) preferably substantially only contains the liquid (3), with no head-space gas above it.

Example 4

The device of this example is identical with that of Example 3, save that the polidocanol in the liquid is replaced with a sodium tetradecylsulfate at 1% vol/vol, all other ingredients being the same.

Example 5

Figure 3:
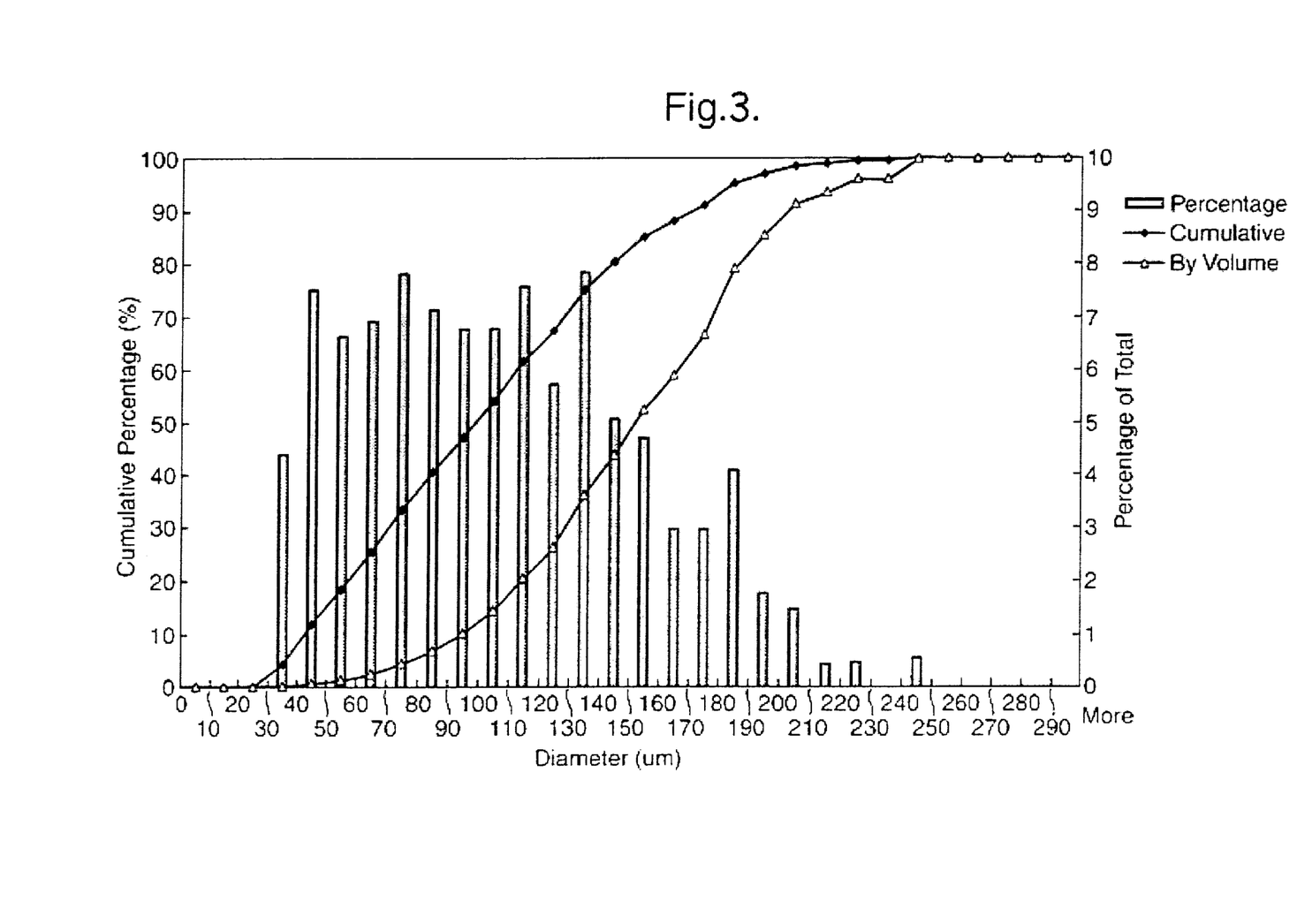
FIG. 3: Is a bar chart and graph illustrating distribution of gas bubble diameter in a preferred 0.13 g/mL oxygen/air/polidocanol microfoam of the fourth aspect.
Figure 4:
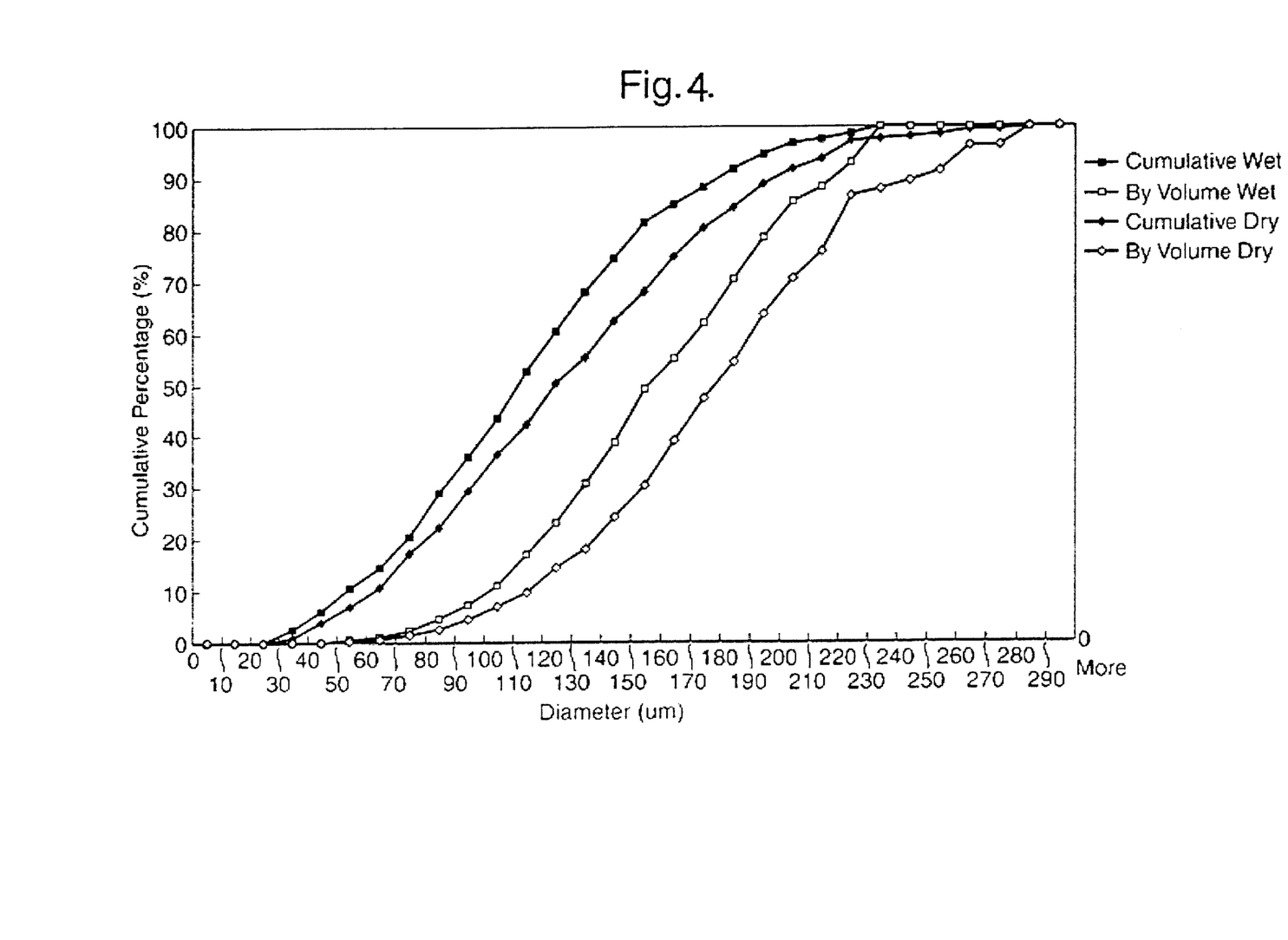
FIG. 4: Is a graph illustrating distribution of gas bubble diameter in microfoams of 0.09 g/mL and 0.16 g/mL of the fourth aspect.
Figure 5:
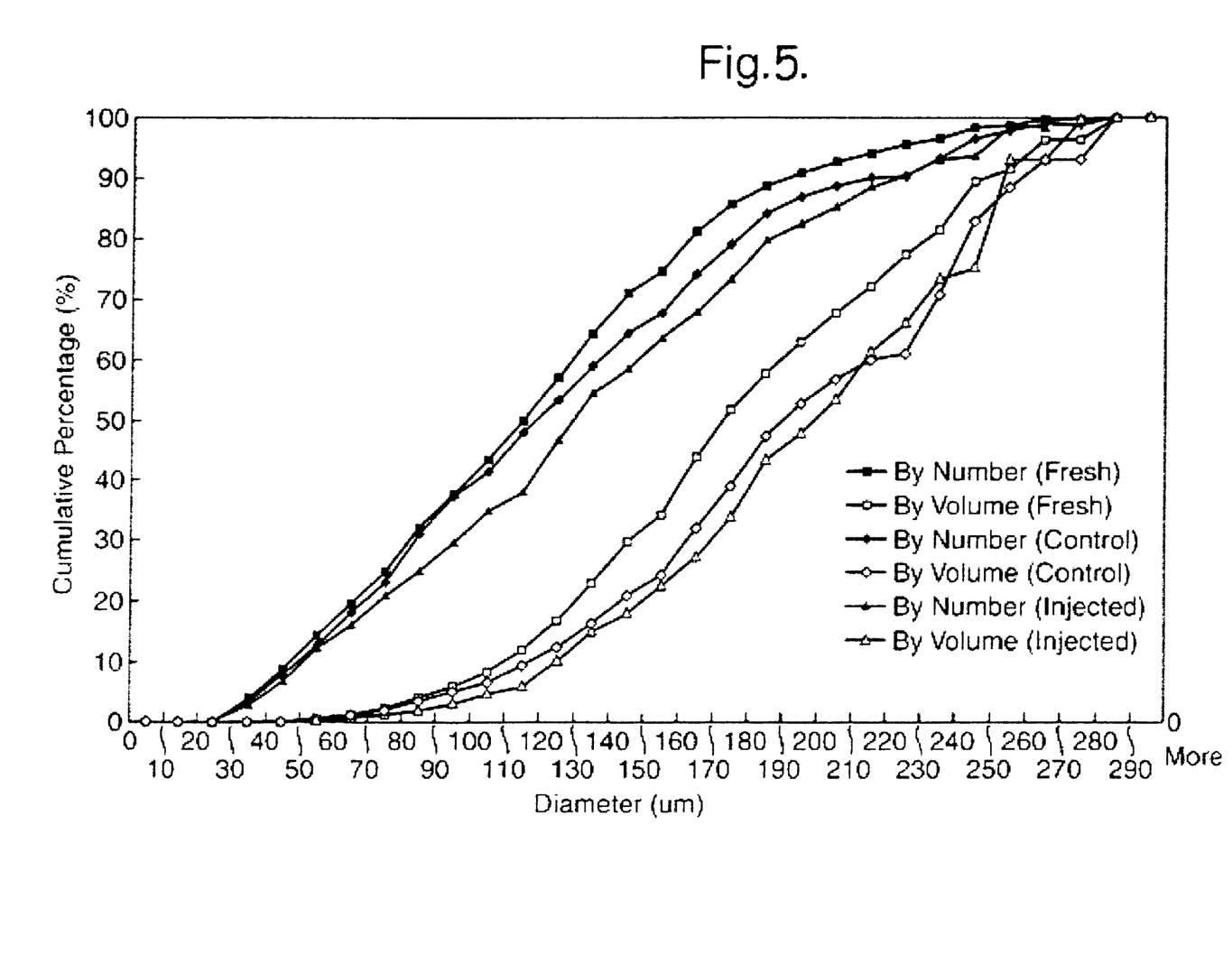
FIG. 5: Is a graph showing the effect of passing a preferred foam of the fourth aspect down a 21 gauge needle as compared to control fresh and similarly aged microfoams.
Figure 6:
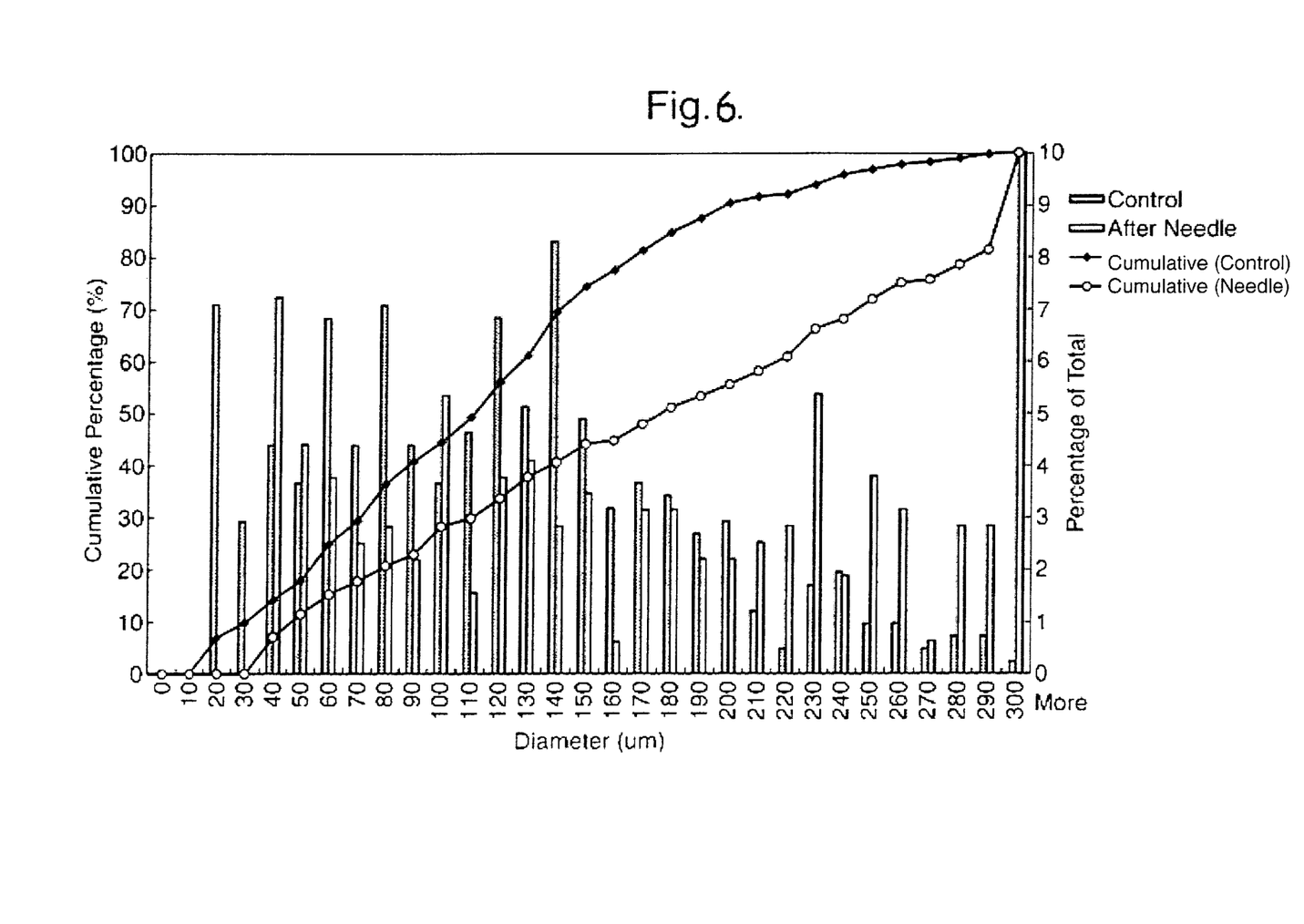
FIG. 6: Is a bar chart and graph showing the effect of passing a 2% vol polidocanol solution dry microfoam of density 0.045 g/mL, such as producible by use of a prior art bubbler device (Swedspray valve, Ecosol insert and head), down a 21 gauge needle.
Figure 7:
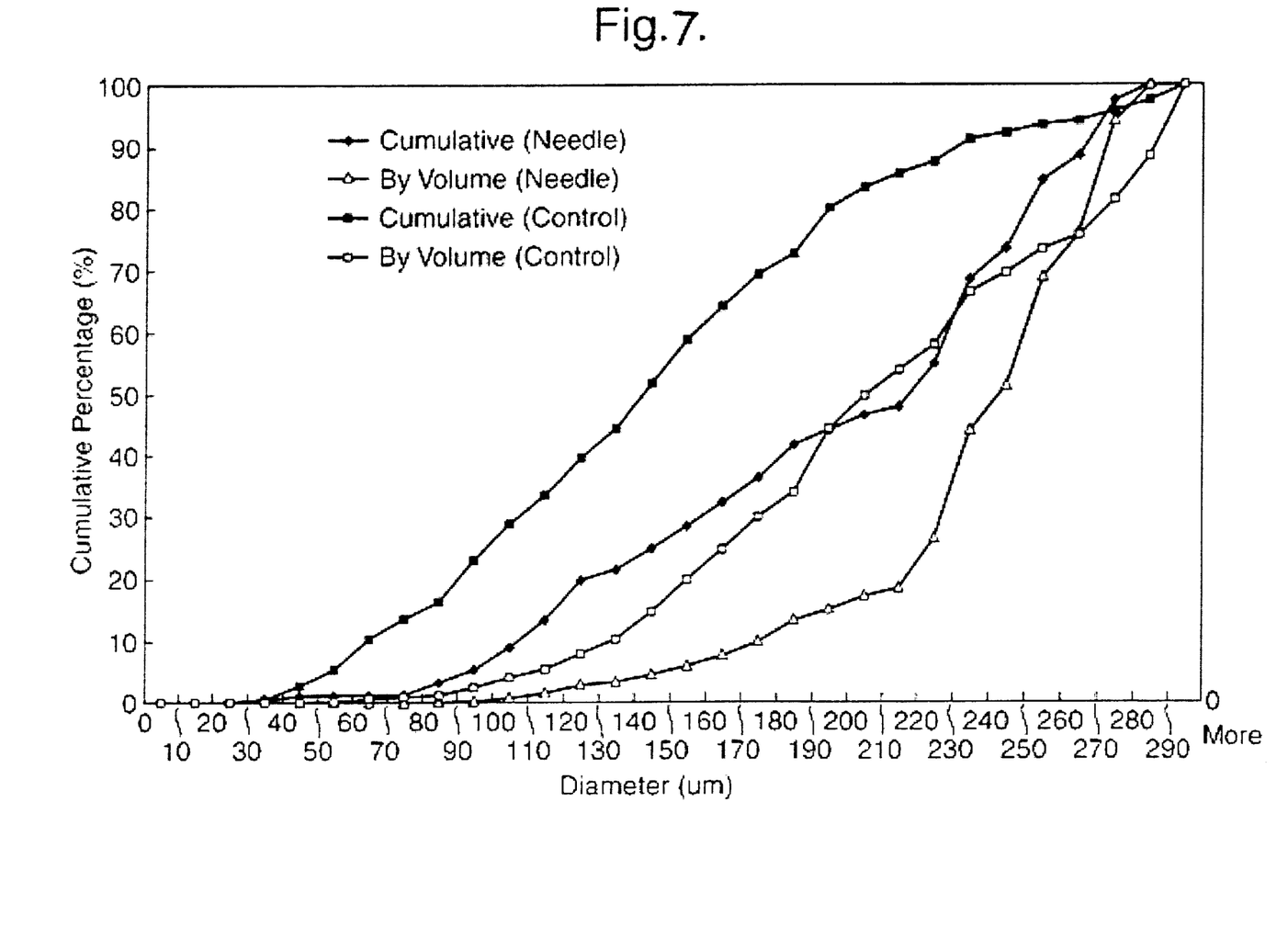
FIG. 7: Is a graph showing the effect of passing a 1% vol polidocanol dry microfoam of 0.045 g/mL such as producible by use of the prior art bubbler device (Swedspray valve, Ecosol insert and head), down a 21 gauge needle.

A microfoam of the invention is produced in a device as described in Example 1, having critical passage and gas mixing dimensions as set out in Example 2 but differing therefrom in that mesh is located in the dispensing cap, downstream of the valve, while gas/liquid mixing occurs in an Precision Valves Ecosol insert device upstream of the valve. The chamber (500 mL) is charged with 15 mL of an aqueous solution containing per 100 mL polidocanol (Kreussler-Germany) (2 mL), 96% ethanol (4 mL) and 55 mmol Phosphate Buffer (pH 7.0) (94 mL) with gas being air overpressured with 1.5 bar 100% oxygen. The characteristics of the microfoam produced on operation of the valve are shown in FIGS. 3 and 4. FIG. 3 shows bubble size distribution immediately after microfoam generation; foam density being 0.138 g/mL. FIG. 4 show bubble size produced with varying ratio of gas to liquid, provided by altering the gas/liquid interface hole size (11a, 11b) to give foams of 0.09 g/mL (diamonds) and 0.16 g/mL (squares). FIG. 5 shows the effect on bubble size distribution of a preferred microfoam (0.13 g/mL) after passage through a 21G needle: Squares show fresh foam, diamonds control foam aged to match injection time and triangles show after pressure through the needle. FIG. 6 shows the effect of passing a microfoam made using a Swedspray device density 0.045 g/mL through the needle. Closed diamonds are control aged while open circles are after needle passage.

Note, when 5% glycerol is added to the formulation, half life was increased to approximately 4 minutes.

Bubble sizes are calculated by taking up foam into a syringe through its luer opening, optionally attaching a 21G needle, and injecting foam between two glass slides that are separated using 23.25 micron diameter beads (e.g. available as microspheres from Park Labs USA). Maxtascan/Global Lab image technique was used to analyze bubble size. Diameters of uncompressed bubbles (Dr) were calculated from diameters of bubbles between slides (Df) using the equation:

$$Dr = \sqrt[3]{\frac{3}{2} Df^2 x}$$

where x is the distance between the slides. These measurements thus are made at ambient temperature and pressure.

It will be realized that bubbles much smaller than 25 µm diameter may be present but not counted. The % figures given with respect to bubble thus relate to bubbles in the range 25 µm and above.

Example 6

Figure 8:
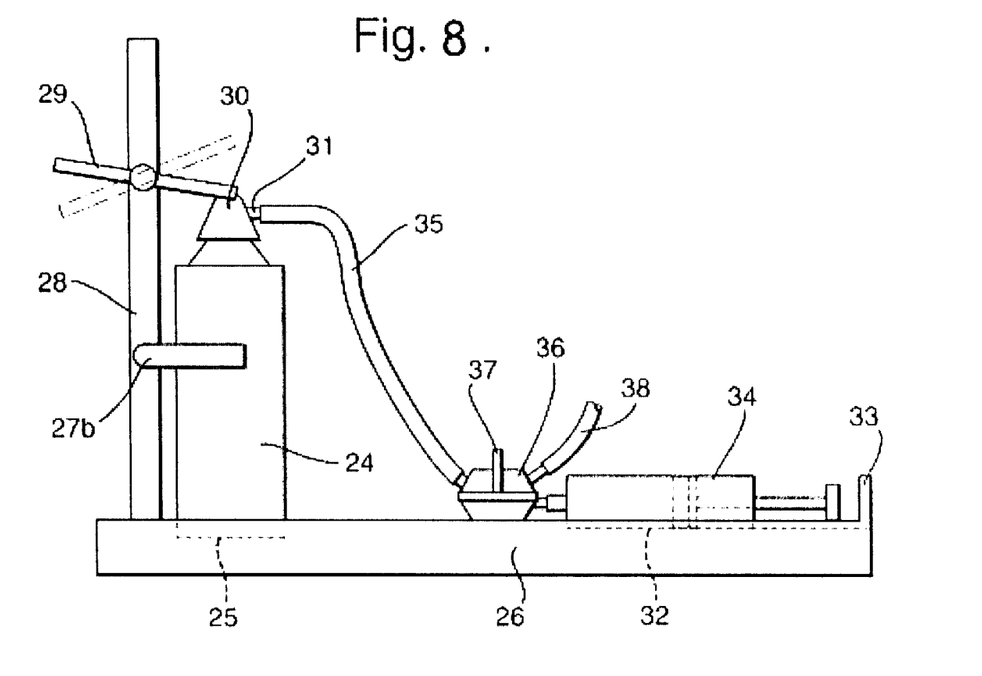
FIG. 8: is an elevation view of a syringe filling device of the fourth aspect.
Figure 9:
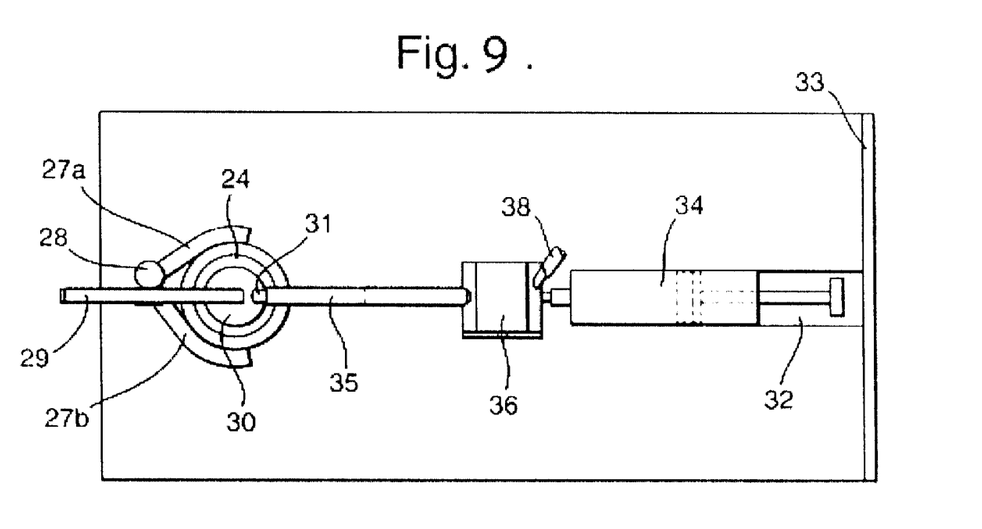
FIG. 9: Is a plan view of the device of FIG. 8.

For filling of a syringe with microfoam of the invention the bottom of a canister of Example 1, 2 or 3 is placed into a receiving recess in the base of a syringe filling device as shown in elevation in FIG. 8 and plan (FIG. 9). Canister (24) is inserted into a 1 cm deep recess (25) in a plastics base element (26), the recess being approximately 1 mm in diameter more than the canister such that a snug fit is provided. The canister is further supported by two resilient fixed arms (27a, 27b), fixed on vertical support rod (28) that deform to receive the canister diameter.

Just above the top of the position of the canister cap in use, the support rod (28) mounts on actuator arm that is lockable between a first actuating position (full lines) an and an off position (dotted lines). In the actuating position the arm depresses the canister actuator cap (30), thus opening the canister valve and causing microfoam to be released.

Also on the base (26) is a recess (32) sized to snugly receive a syringe (34) with its plunger. A stop element (33) is provided that is positioned such that on filling the plunger is limited in its range of longitudinal movement such that the syringe cannot be overfilled.

A flexible transparent plastic tube (35), inert to the sclerosant foam, is attached to the canister outlet nozzle (31) in use and is fixed to a three way valve (36) affixed to the base (26). The valve is operated by turning a tap (37) to one of three positions: (a) valve shut—no microfoam passage (b) valve open to waste (38) whereby any microfoam that by visual inspection of the contents of tube (35) appears unsuitable, is vented and (c) valve open to syringe, whereby a set amount of microfoam passes through the syringe luer and fills it until the syringe plunger abuts the stop (33).

Example 7

20 mL microfoam of Example 6 is loaded into a 20 mL syringe using the device of Example 6 and the syringe disengaged from the device. A 19 gauge needle is attached either directly to the syringe luer fitting or via a catheter. The microfoam is administered into to a varicose vein while its advance and final position is monitored using a hand held ultrasound scanner such that the fresh foam is restricted in location to the vein being treated. After between 1 and 5 minutes the vein contracts and subsequently becomes fibrosed.

What is claimed is:

1. A method for producing a microfoam suitable for use in sclerotherapy of blood vessels said microfoam comprising gas bubbles in which at least 50% by number of the gas bubbles of 25 µm diameter and above are of no more than 200 µm diameter and at least 95% of these gas bubbles are no more than 280 µm diameter, said method comprising passing a mixture of a physiologically acceptable blood dispersible gas capable of being substantially completely dissolved in or absorbed by blood and an aqueous sclerosant liquid through one or more passages having at least one cross-sectional dimension of from 0.1 to 30 µm, the ratio of gas to liquid being controlled such that a microfoam is produced having a density of between 0.07 g/mL to 0.19 g/mL and has a half-life of at least 2 minutes, to produce said microfoam, said microfoam being formed without the prior step of beating with a brush.

2. A method as described in claim 1 wherein the gas/liquid ratio in the mixture is controlled such that the density of the microfoam is 0.09 g/mL to 0.16 g/mL.

3. A method as claimed in claim 1 wherein at least 50% by number of the gas bubbles of 25 µm diameter and above are of no more than 150 µm diameter and at least 95% of these gas bubbles are no more than 250 µm diameter.

4. A method as claimed in claim 1 wherein the mixture of gas and sclerosant liquid is in the form of an aerosol, dispersion of bubbles in liquid or macrofoam.

5. A method as claimed in claim 1 wherein the ratio of gas to liquid used in the mixture is 1 gram sclerosant liquid to form 6.25 to 14.3 volumes of gas as standard temperature and pressure.

6. A method as claimed in claim 1 wherein the physiologically acceptable blood dispersible gas comprises over 50% volume of carbon dioxide and/or oxygen.

7. A method as claimed in claim 1 wherein the aqueous sclerosant liquid is a solution of polidocanol or sodium tetradecylsulfate (STS) in an aqueous carrier.

8. A method as claimed in claim 7 wherein the carrier comprises a saline solution.

9. A method as claimed in claim 1 wherein the cross-sectional dimension is diameter and the one or more passages through which the gas and liquid mixture are passed to produce the microfoam have diameter of from 5 µm to 25 µm.

10. A method as claimed in claim 9 wherein the passages are of from 10 µm to 20 µm diameter and are openings in a mesh or screen placed perpendicular to the direction of flow of the gas/liquid mixture.

11. A method as claimed in claim 9 wherein the passages are provided as multiple openings in one or more elements through which the mixture flows.

12. A method as claimed in claim 11 wherein the multiple openings provide a 2% to 65% open area in the one or more elements.

13. A method as claimed in claim 11 wherein the element comprises porous material and a number said elements are arranged sequentially such that the gas and liquid pass through the passages of each element.

14. A method as claimed in claim 13 wherein the elements are spaced and are placed along the direction of flow of the mixture in series.

15. A method as claimed in claim 1 wherein the mixture of gas and liquid is passed through the same passage or passages a number of times.

16. A method as claimed in claim 1 wherein the gas is pressurized to 0.01 to 9 bar over atmospheric pressure.

17. A method as claimed in claim 16 wherein the gas is pressurized at 0.1 to 3 bar over atmospheric pressure.

18. A method for producing a microfoam suitable for use in sclerotherapy of blood vessels said microfoam comprising gas bubbles in which at least 50% by number of gas bubbles of 25 µm diameter and above are of no more than 200 µm diameter and at least 95% of these gas bubbles are no more than 280 µm diameter, said method comprising passing a mixture of a physiologically acceptable blood dispersible gas capable of being substantially completely dissolved in or absorbed by blood and an aqueous sclerosant liquid through one or more passages having at least one cross-sectional dimension of from 0.1 to 30 µm, wherein said mixture of gas and sclerosant liquid is not in the form of a microfoam, the ratio of gas to liquid being controlled such that a microfoam is produced having a density of between 0.07 g/mL to 0.19 g/mL and has a half-life of at least 2 minutes, to produce said microfoam.

19. A method for producing a microfoam suitable for use in sclerotherapy of blood vessels and microfoam comprising gas bubbles in which at least 50% by number of the gas bubbles of 25 mm diameter and above are of no more than 200 mm diameter and at least 95% of these gas bubbles are no more than 280 mm diameter, said method comprising passing a mixture of a physiologically acceptable blood dispersible gas capable of being substantially completely dissolved in or absorbed by blood and an aqueous sclereosant liquid through one or more passages having at least one cross-sectional dimension of from 0.1 to 30 mm, said mixture of gas and sclerosant liquid being in the form of a dispersion of bubbles in liquid or a macrofoam, the ratio of gas to liquid being controlled such that a microfoam is produced having a density of between 0.07 g/mL to 0.19 g/mL and has a half-life of at least 2 minutes, to produce said microfoam.

\* \* \* \* \*

UNITED STATES PATENT AND TRADEMARK OFFICE
CERTIFICATE OF CORRECTION

PATENT NO. : 6,572,873 B1  Page 1 of 1
APPLICATION NO. : 09/718094
DATED : June 3, 2003
INVENTOR(S) : Tariq Osman et al.

It is certified that error appears in the above-identified patent and that said Letters Patent is hereby corrected as shown below:

In claim 19, column 18, line 32, "25 mm diameter" should read --25 µm diameter--.

In claim 19, column 18, line 33, "200 mm diameter" should read --200 µm diameter--.

In claim 19, column 18, line 34, "280 mm diameter" should read --280 µm diameter--.

In claim 19, column 18, line 39, "30 mm," should read --30 µm,--.

Signed and Sealed this

Twenty-third Day of June, 2009

JOHN DOLL
*Acting Director of the United States Patent and Trademark Office*